(12) United States Patent
Roth et al.

(10) Patent No.: US 7,935,485 B2
(45) Date of Patent: May 3, 2011

(54) GENETIC POLYMORPHISMS FOR IDENTIFYING INDIVIDUALS AT RISK FOR DRUG-INDUCED VESTIBULAR DYSFUNCTION

(75) Inventors: Stephen M. Roth, Columbia, MD (US); John J. Jeka, Sevema Park, MD (US); Scott M. Williams, Nashville, TN (US)

(73) Assignee: University of Maryland College Park, College Park, MD (US)

( * ) Notice: Subject to any disclaimer, the term of this patent is extended or adjusted under 35 U.S.C. 154(b) by 221 days.

(21) Appl. No.: 12/079,860

(22) Filed: Mar. 28, 2008

(65) Prior Publication Data

US 2009/0202996 A1 Aug. 13, 2009

Related U.S. Application Data

(60) Provisional application No. 60/909,157, filed on Mar. 30, 2007.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6; 435/91.2; 536/23.5; 536/24.31; 536/24.33

(58) Field of Classification Search .......... None
See application file for complete search history.

(56) References Cited

U.S. PATENT DOCUMENTS 6,582,908 B2 * 6/2003 Fodor et al. .............. 506/9

OTHER PUBLICATIONS

Roth et al. FASEB Journal. Apr. 28-May 2, 2007. 21(5): pA415.*
Kaminker et al (Cancer Research. 2007. 67(2): 465-473, and supplemental content.*
NCBI Database, National Center for Biotechnology Information, National Library of Medicine, NIH, (Bethesda, MD, USA) GenBank Accession No. L10698, Aug. 13, 1993.*
NCBI Database, National Center for Biotechnology Information, National Library of Medicine, NIH, (Bethesda, MD, USA) GenBank Accession No. AF053541, Apr. 16, 1999.*
NCBI Database, National Center for Biotechnology Information, National Library of Medicine, NIH, (Bethesda, MD, USA) GenBank Accession No. U21689, Jan. 6, 1998.*
Mitsuhashi et al. Journal of Laboratory Analysis. 1996. 10: 285-293).*

* cited by examiner

*Primary Examiner* — Carla Myers
(74) *Attorney, Agent, or Firm* — Pratt & Associates, Inc.; Sana A. Pratt

(57) ABSTRACT

In this application is described the identification of genetic variants that contribute to susceptibility to drug-induced vestibular dysfunction, more particularly, GM-induced vestibular dysfunction. Methods, compositions and kits for determining whether an individual has susceptibility for drug-induced vestibular dysfunction are disclosed.

4 Claims, 2 Drawing Sheets

GENETIC POLYMORPHISMS FOR IDENTIFYING INDIVIDUALS AT RISK FOR DRUG-INDUCED VESTIBULAR DYSFUNCTION

This application claims benefit of priority from Provisional Application Ser. No. 60/909,157 filed on Mar. 30, 2007.

This invention was made with government support under NIH grant R21NS046021 awarded by the National Institutes of Health. The Government has certain rights in the invention.

INTRODUCTION

The irreparable ototoxic potential of chemotherapy agents and aminoglycoside antibiotics, such as gentamicin (GM), is well known (Schacht, J. 1999, Ann. N.Y. Acad. Sci. 884, 125-130). A significant fraction (6-16%) of individuals who receive treatment with such drugs every year experience hearing loss or vestibular dysfunction without visual or somatosensory involvement (N. Fischel-Ghodsian, 1999, Ann. N.Y. Acad. Sci. 884, 99-109; Lerner et al., 1986, Am. J. Med. 80, 98-104; Rinne et al., 1998, J. Neurol. 245, 314-321). Remarkably, most patients who experience vestibular dysfunction do not also experience hearing loss, indicating different susceptibilities (Fischel-Ghodsian, 1999, supra; Lerner et al., 1986, supra; Rinne et al., 1998, supra). For example, of 53 patients with bilateral vestibular failure, nine were the result of drug-induced ototoxicity, but only one patient presented with hearing impairment resulting from ototoxicity (Rinne et al., 1998, supra). Similarly, Lerner et al. (1986, supra) observed auditory dysfunction in three of 33 GM-treated patients and vestibular dysfunction in three different patients, with no patients exhibiting both deficits. Moreover, intra-tympanic administration of GM is used specifically for the treatment of vertigo for Meniere's disease, and hearing loss, although not unexpected, does not occur in most patients following this treatment (Dobie et al., 2006, Arch Otolaryngol Head Neck Surg 132, 253-257; Smith et al., 2006, J. Laryngol Otol 120, 730-735).

While specific genetic susceptibility has not been observed for drug-induced vestibular dysfunction, genetic susceptibility to hearing loss associated with drug-induced ototoxicity has been established (Bitner-Glindzicz et al., 2007, BMJ 335, 784-785). The maternal heritability of hearing loss in response to various aminoglycoside antibiotics has been established in multiple families, including the identification of mutations in the mitochondrially encoded 12S RNA (MTRNR1) gene (Fischel-Ghodsian, 1999, supra). The m.1555A>G mutation in the 12S rRNA gene has been shown to explain up to 30% of hearing loss cases in relation to drug therapy (Fischel-Ghodsian, 1999, supra). Remarkably, this same mutation is not associated with loss of vestibular function (Braverman et al., 1996, Arch. Otolaryngol. Head Neck Surg. 122, 1001-1004), although it has not been examined in a large cohort. Importantly, the only specific environmental risk factors known to contribute to GM-induced ototoxicity are age (i.e., higher risk for infants and children) and dose/duration of treatment (Begg and Barclay, 1995, Br. J. Clin. Pharmacol. 39, 597-603).

GM and other aminoglycosides are not metabolized by the body, so all effects resulting from GM are specific to the drug itself (Begg and Barclay, 1995, supra), rather than to a drug metabolite. Following drug entry into the inner ear, several studies now show that the production of nitric oxide (NO) and related reactive oxygen species (ROS) is an important factor in GM-related ototoxicity (Schacht, J. 1999, supra; Takumida and Anniko, 2002, Acta Otolaryngol. 122, 20-15; Takumida et al., 1999, ORL J. Otorhinolaryngol. Relat. Spec. 61, 63-70; Ylikoski et al., 2002, Hearing Res. 163, 71-81). The presence of ROS scavengers and glutathione synthase inhibitors has been shown to reduce GM toxicity (Song and Schacht, 1996, Hearing Res. 94, 809-814; Takumida and Anniko, 2002, supra; Takumida et al., 2003, Acta Otolaryngol. 123, 8-13). Moreover, the use of neurotrophic factors (important for cell survival and regeneration in the inner ear) alone (Lopez et al., 1999, Am. J. Otol. 20, 317-324; Zheng et al., 1995, J. Neurobiol. 330-340) and in combination with ROS scavengers (Takumida and Anniko, 2002, supra; Takumida et al., 2003, supra) also reduces GM-related ototoxicity. Based on this large body of evidence, Takumida et al. (2002, supra) and others (Agerman et al., 1999, Ann. N.Y. Acad. Sci. 884, 131-142) have proposed a model of GM-induced ototoxicity centered on NO and ROS. Most recently, isosorbide was shown to delay GM-induced vestibular hair cell death by inhibiting NO and ROS production (Takumida and Anniko, 2005, ORL J. Otorhinolaryngol. Relat. Spec. 67, 276-281).

In order to understand the mechanisms leading to this disorder and to develop improved diagnosis and therapeutic treatment, identifying genes involved in GM-induced vestibular dysfunction is needed.

SUMMARY OF THE INVENTION

In the present invention, the inventors sought to identify genetic variants that contribute to susceptibility to drug-induced vestibular dysfunction, more particularly GM-induced vestibular dysfunction. Candidate genes were primarily selected based on the proposed oxidative stress model of GM-induced ototoxicity (e.g., brain-derived neurotrophic factor; endothelial nitric oxide synthase; glutathione S-transferases). The inventors also examined myosins VI, VIIA and XVA as candidate genes, as they have all been indicated as candidate genes for vestibular dysfunction given their importance for hair cell structure and function Friedman, et al., 2000, Adv. Otorhinolaryngol. 56, 131-144; Melchionda et al., 2001, Am. J. Hum. Genet. 69, 635-640) and myosin VIIA has been shown to be required for GM accumulation in mouse hair cells (Richardson et al., 1997, J. Neurosci. 17, 9509-9519).

Through both single gene and multi-dimensionality reduction (MDR) analyses, the inventors have demonstrated that missense polymorphisms in three genes, consisting of nitric oxide synthase 3, (NOS3) (p.Glu298Asp), Glutathione S-transferase (GST) GSTZ1 (p.Lys32Glu), and GSTP1 (p.Ile105Val), provided the highest predictive model for GM-induced vestibular dysfunction. All three genes are related to nitric oxide (NO) production and reactive oxygen species (ROS) inactivation.

The invention thus discloses novel targets for diagnosis and therapeutic intervention for drug-induced vestibular dysfunction, more particularly, GM-induced vestibular dysfunction. These polymorphisms could produce sensitivity to other commonly used aminoglycoside antibiotics for the treatment of infections caused by Gram-negative bacteria. For example, antibacterial aminoglycosides include, without limitation, neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin and the like. (see Goodman and Gilman's The Pharmacological Basis of Therapeutics, 6th ed., A. Goodman and Gilman et al., eds; Macmillan Publishing Co., Inc., New York, pp. 1169-71 (1980)).

These polymorphisms also potentially could produce sensitivity to other therapeutic drugs and chemicals such as:

antineoplastic agents, contaminants in foods or medicines, and environmental and industrial pollutants. For example, quinine and its analogs, salicylate and its analogs, and loop-diuretics. Ototoxicity is also a serious dose-limiting side-effect for cisplatin and its analogs, a platinum coordination complex, that has proven effective on a variety of human cancers including testicular, ovarian, bladder, and head and neck cancer. Cisplatin damages vestibular systems.

As described herein, missense polymorphisms in three genes, Nitric oxide synthase 3, hereinafter NOS3, Glutathione S-transferase Z1, hereinafter, GSTZ1, and Glutathione S-transferase P1, hereinafter GSTP1, have been identified as playing a major role in drug-induced vestibular dysfunction, more particularly, GM-induced vestibular dysfunction.

Therefore, in one aspect, the invention includes materials and methods for identifying or diagnosing a person or screening for increased risk (susceptibility) to drug-induced vestibular dysfunction, more particularly, GM-induced vestibular dysfunction or other conditions based on NOS3, GSTZ1 and/or GSTP1 polymorphisms that can be assayed from their DNA, RNA, or protein.

In one aspect, the invention is a method of screening a human subject for susceptibility or elevated risk for drug-induced vestibular dysfunction, more particularly, GM-induced vestibular dysfunction or other related ototoxic events by assaying nucleic acid from the subject for one or more polymorphisms, wherein the presence of a polymorphism in said nucleic acid sequence indicates that said individual has an increased predisposition to GM-induced vestibular dysfunction compared to an individual without the polymorphism.

In one aspect, the method comprises detecting in a sample from the subject the presence of an alteration in the NOS3 gene or in the ENOS protein, the presence of said alteration being indicative of the presence or predisposition to vestibular dysfunction. The NOS3 polymorphism by itself is a reasonable target based on this study, and provides only a slightly less strong prediction of disease compared to the three-gene combination of NOS3, GSTZ1 and GSTP1. As shown in Table 3, NOS3 by itself provides 57% accuracy, while the 3-gene combination provides 64% accuracy. Suitably, the polymorphism is a guanine to thymine change at position 893 of the NOS3 gene, producing a glutamine to asparagine change at amino acid 298 of the translated protein ENOS, In another aspect, the method comprises detection of an alteration in a three-gene combination comprising, a guanine to thymine change at position 893 of the NOS3 gene, producing a glutamine to asparagine change at amino acid 298 of the translated protein ENOS, and/or a adenine to guanine change at position 312 of GSTP1 gene producing an isoleucine to valine change at amino acid 105 of the GSTP1 protein and/or an adenine to guanine change at position 94 producing a lysine to glutamine change at amino acid 32 of the GST Zeta 1 protein. Accession numbers for sequences of these genes are found in Table 1.

In another aspect, the invention provides a kit for identifying a predisposition to drug-induced vestibular dysfunction, more particularly, GM-induced vestibular dysfunction for use in the method of the aforementioned aspects, said kit comprising one or more primers, probes and/or antibodies and optionally, one or more other reagents for identifying said polymorphism(s). By antibody is meant a "specific" antibody which binds specifically to the altered polypeptide and essentially does not bind specifically the wild-type polypeptide or the binding of the two forms can be discriminated.

In a particular embodiment, the kit comprises (a) primers for nucleic acid sequence amplification of at least a fragment of a human NOS3 gene that encodes codon 298 of an ENOS protein; and/or (b) primers for nucleic acid sequence amplification of at least a fragment of a human GSTP1 gene that encodes codon 105 of a GST Pi protein; and/or (c) primers for nucleic acid sequence amplification of at least a fragment of a human GSTZ1 gene that encodes codon 32 of a GST Zeta 1 protein.

Suitably, according to the aforementioned aspects, said individual is a male or female human.

The invention also pertains to methods of treatment (prophylactic and/or therapeutic) for certain diseases and conditions treated with an aminoglycoside antibiotic, specifically gentamicin, wherein the presence in a subject of a polymorphism selected from the group consisting of (i) a guanine to thymine change at position 893 of the NOS3 gene, producing a glutamine to asparagine change at amino acid 298 of the ENOS protein, (ii) an adenine to guanine change at position 312 of GSTP1 gene producing an isoleucine to valine change at amino acid 105 of the GST Pi protein, and (iii) an adenine to guanine change at position 94 of human GSTZ1 gene producing a lysine to glutamine change at amino acid 32 of the GST Zeta 1 protein, identifies the subject as having a susceptibility to GM-induced vestibular dysfunction, and administration of a non-aminoglycoside antibiotic is preferred.

DETAILED DESCRIPTION

Figure 1:
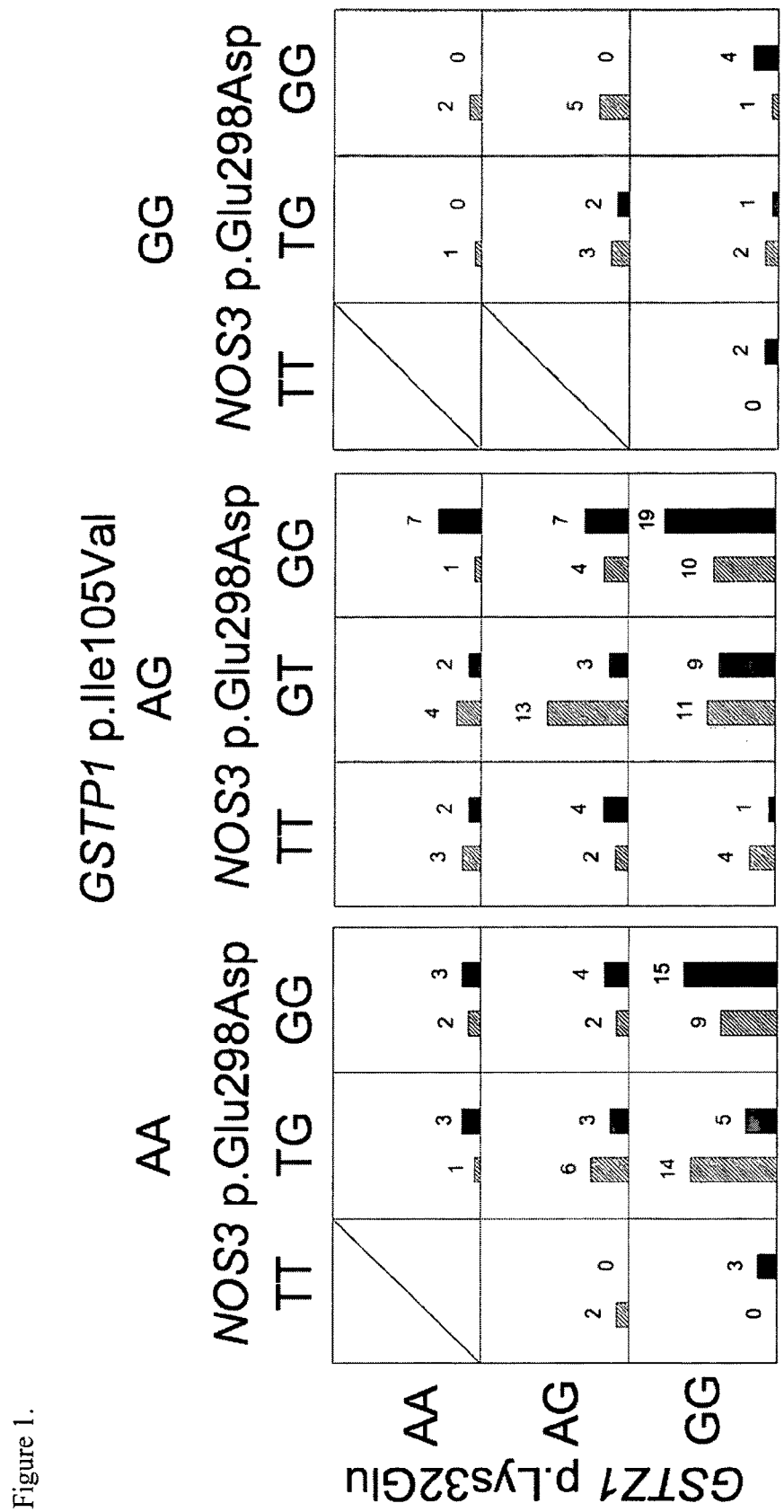
FIG. 1. A graphical representation of the three-gene MDR model with 64% prediction accuracy. Each cell shows the number of cases (left side of each cell; hatched bars) and controls (right side of each cell; solid bars) carrying that combination of the three genotypes from the GSTZ1 p.Lys32Glu, GSTP1 p.Ile105Val, and NOS3 p.Glu298Asp polymorphisms. Shaded cells are higher-risk, based on the proportion of cases vs. controls carrying that particular genotype combination.

As used herein, the terms below and variations thereof shall be defined as follows, unless otherwise indicated:

Throughout this specification "susceptibility", "predisposed and predisposition" in the context of drug-induced vestibular dysfunction, more particularly, GM-induced vestibular dysfunction means that an individual has an increased probability of suffering from vestibular dysfunction and includes situations where said individual is not yet exhibiting clinical symptoms of vestibular dysfunction and where said individual is already displaying vestibular dysfunction symptoms.

The term "gene" is used herein as a discrete nucleic acid unit or region that may comprise one or more of introns, exons, open reading frames, splice sites, untranslated regions, and regulatory sequences such as promoters and polyadenylation sequences.

The term "polymorphism" is used herein to indicate any nucleotide sequence variation in an allelic form of a gene that occurs in a human population. This term encompasses mutation, insertion, deletion and other like terms that indicate specific types of polymorphisms.

"Aminoglycoside antibiotics", indicates, as implied by the generic name for the family, all the aminoglycoside antibiotics containing aminosugars in glycosidic linkage. The aminoglycosides are used primarily to treat infections caused by gram-negative bacteria and, for instance, in combination with penicillins for the synergistic effects. An aminoglycoside antibiotic is selected from the group consisting of neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin.

Aminoglycoside antibiotics are generally utilized as broad spectrum antimicrobials effective against, for example, gram-positive, gram-negative and acid-fast bacteria. Susceptible microorganisms include *Escherichia* spp., *Haemohilus* spp., *Listeria* spp., *Pseudomonas* spp., *Nocardia* spp., *Yersinia* spp., *Klebsiella* spp., *Enterobacter* spp., *Salmonella* spp., *Staphyloccocus* spp., *Streptococcus* spp., *Mycobacteria* spp., *Shigella* spp., and *Serratia* spp. Ototoxicity is a dose-limiting side-effect of antibiotic administration.

In one embodiment, the present invention provides for determination of a susceptibility or predisposition to drug-induced vestibular dysfunction, more particularly, GM-induced vestibular dysfunction, according to whether an individual has a polymorphism in any of three genes, the polymorphism can be a guanine to thymine change at position 893 of the NOS3 gene, producing a glutamine to asparagine change at amino acid 298 of the translated protein ENOS, and/or an adenine to guanine change at position 312 of GSTP1 gene producing an isoleucine to valine change at amino acid 105 of the GST Pi protein and/or an adenine to guanine change at position 94 of the GSTZ1 gene producing a lysine to glutamine change at amino acid 32 of the GST Zeta 1 protein. The single gene NOS3 polymorphism by itself provides a strong prediction of susceptibility to disease (57% accuracy) compared to a slightly stronger prediction (64% accuracy) from the three-gene combination.

Additionally, other polymorphisms which may be indicative include the polymorphism a thymine to a cytosine change at position −813 in the promoter region of the NOS3 gene.

It will therefore be appreciated that by isolating a nucleic acid corresponding to at least a fragment of a gene that potentially includes the polymorphism, a determination can be made as to whether an individual is predisposed to drug-induced vestibular dysfunction, more particularly, GM-induced vestibular dysfunction.

For the purposes of this invention, by "isolated" is meant material that has been removed from its natural state or otherwise been subjected to human manipulation. It is not necessary for isolated material to be substantially or essentially free from components that normally accompany it in its natural state, if the target is detectable without further purification. Isolated material may be in native or recombinant form.

Any specimen nucleic acid, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, which may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The nucleotide sequence to be amplified, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA, as long as the target nucleic acid sequence is included. The altered nucleotide sequence, or the corresponding region of the nucleotide sequence of a normal individual not susceptible to drug-induced vestibular dysfunction, is referred to as the "target nucleic acid sequence".

By "protein" is meant an amino acid polymer. The amino acids may be natural or non-natural amino acids, D- or L-amino acids as are well understood in the art.

A "peptide" is a protein having less than fifty (50) amino acids.

A "polypeptide" is a protein having fifty (50) or more amino acids.

The term "nucleic acid" as used herein designates single- or double-stranded mRNA, RNA, cRNA and DNA inclusive of cDNA and genomic DNA and DNA-RNA hybrids.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

The terms "anneal", "hybridize" and "hybridization" are used herein in relation to the formation of bimolecular complexes by base-pairing between complementary or partly-complementary nucleic acids in the sense commonly understood in the art. It should also be understood that these terms encompass base-pairing between modified purines and pyrimidines (for example, inosine, methylinosine and methyladenosine) and modified pyrimidines (for example thiouridine and methylcytosine) as well as between A, G, C, T and U purines and pyrimidines. Factors that influence hybridization such as temperature, ionic strength, duration and denaturing agents are well understood in the art, although a useful operational discussion of hybridization is provided in to Chapter 2 of CURRENT PROTOCOLS IN MOLECULAR BIOLOGY (Eds. Ausubel et al. John Wiley & Sons NY, 2000), particularly at sections 2.9 and 2.10.

In one aspect, the present invention provides methods for determining whether an individual is predisposed of susceptible to drug-induced vestibular dysfunction, more particularly, GM-induced vestibular dysfunction.

Suitably, said individual is a male or female human.

Such methods may be used independently of clinical diagnosis or may be used in conjunction therewith to confirm or assist clinical diagnosis and prescription of medication for treatment of infections otherwise requiring aminoglycoside antibiotics.

It will also be appreciated that detection of the polymorphisms in any of three genes may be performed independently or together, in any combination. The polymorphism to be detected can be a guanine to thymine change at position 893 of the NOS3 gene, producing a glutamine to asparagine change at amino acid 298 of the translated protein ENOS, and/or an adenine to guanine change at position 312 of GSTP1 gene producing an isoleucine to valine change at amino acid 105 of the GST Pi protein and/or an adenine to guanine change at position 94 of the GSTZ1 gene producing a lysine to glutamine change at amino acid 32 of the GST Zeta 1 protein. Additionally, other polymorphisms which may be detected include the polymorphism a thymine to a cytosine change at position −813 in the promoter region of the NOS3 gene. In a particular aspect, the presence of any of the gene polymorphisms in an individual are indicative of an increased predisposition to GM-induced vestibular dysfunction compared to a subject without said polymorphism. The NOS3 893 site by itself provides only a slightly less strong prediction of disease compared to the three-gene combination. As shown in Table 3, NOS3 893 by itself provides 57% accuracy, while the 3-gene combination provides 64% accuracy, and potentially more information.

Generally, the methods of the invention are nucleic acid-based methods, given that the polymorphisms described herein have initially been identified and confirmed at the nucleic acid level.

Furthermore, the −813 of the NOS3 gene polymorphism with a thymine to a cytosine change is in the promoter region, hence protein-based analysis of this polymorphism is not contemplated as a preferred form of the invention. However, it is postulated that the other polymorphisms listed may affect protein expression, hence protein based methods of detection may be used according to the present invention.

Such methods are well known in the art and include western blotting, ELISA, two dimensional protein profiling, protein arrays, immunoprecipitation, radioimmunoassays and radioligand binding, although without limitation thereto.

With regard to nucleic acid detection, an isolated nucleic acid corresponding to at least a fragment of a gene may be isolated from any appropriate source of nucleic acid, such as lymphocytes or any other nucleated cell type, preferably obtainable by a minimally-invasive method.

The isolated nucleic acid fragment may be in the form of genomic DNA, RNA or cDNA reverse-transcribed from isolated RNA.

Typically, in certain embodiments fragments may have at least 9, 15, 20, 50 or up to 80 contiguous nucleotides (such as oligonucleotide primers and probes). In other embodiments, fragments may have 200, 300, 500 or more contiguous nucleotides (such as PCR amplification products).

Suitably, in one form the fragment comprises a guanine to thymine change at position 893 of the NOS3 gene.

Suitably, in another form the fragment comprises an adenine to guanine change at position 312 of GSTP1 gene.

Suitably, in yet another form the fragment comprises an adenine to guanine change at position 94 of GSTZ1 gene.

Additionally, in another form, the fragment comprises a thymine to a cytosine change at position −813 in the promoter region of the NOS3 gene.

A further object of this invention is a vector comprising a nucleic acid encoding a polypeptide comprising an alteration according to the present invention, for example, an NOS3 gene, producing a glutamine to asparagine change at amino acid 298 of the translated protein ENOS, and/or a adenine to guanine change at position 312 of GSTP1 gene producing an isoleucine to valine change at amino acid 105 of the GST Pi protein and/or an adenine to guanine change at position 94 of the GSTZ1 gene producing a lysine to glutamine change at amino acid 32 of the GST Zeta 1 protein. The vector may be a cloning vector or, more preferably, an expression vector, i.e., a vector comprising regulatory sequences causing expression of the altered polypeptide from said vector in a competent host cell.

These vectors can be used to express a polypeptide according to the present invention in vitro, ex vivo or in vivo, to create transgenic or "Knock Out" non-human animals, to amplify the nucleic acids, to express antisense RNAs, etc.

The vectors of this invention typically comprise a coding sequence according to the present invention operably linked to regulatory sequences, e.g., a promoter, a polyA, etc. The term "operably linked" indicates that the coding and regulatory sequences are functionally associated so that the regulatory sequences cause expression (e.g., transcription) of the coding sequences. The vectors may further comprise one or several origins of replication and/or selectable markers. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like.

The vector may be a plasmid, a virus, a cosmid, a phage, a BAC, a YAC, etc. Plasmid vectors may be prepared from commercially available vectors such as pBluescript, pUC, pBR, etc. Viral vectors may be produced from baculoviruses, retroviruses, adenoviruses, AAVs, etc., according to recombinant DNA techniques known in the art.

A further object of the present invention resides in a recombinant host cell comprising a recombinant gene according to the present invention or a vector as defined above. Suitable host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). More particularly, the invention contemplates intratympanic cells.

The present invention also relates to a method for producing a recombinant host cell expressing a polypeptide comprising an alteration according to the present invention, said method comprising (i) introducing in vitro or ex vivo into a competent host cell a recombinant nucleic acid or a vector as described above, (ii) culturing in vitro or ex vivo the recombinant host cells obtained and (iii), optionally, selecting the cells which express and/or secrete said polypeptide.

Such recombinant host cells can be used for the production of polypeptides according to the present invention, as well as for screening of active molecules, as described below. Such cells may also be used as a model system to study drug-induced vestibular dysfunction, more particularly GM-induced vestibular dysfunction and/or hearing disorders. These cells can be maintained in suitable culture media, such as DMEM, RPMI, HAM, etc., in any appropriate culture device (plate, flask, dish, tube, pouch, etc.).

The invention now provides diagnosis methods based on a monitoring of alteration at any of the NOS3, GSTP1 and GSTZ1 loci in a subject. Within the context of the present invention, the term "diagnosis" includes the detection, monitoring, dosing, comparison, etc., at various stages, including early, pre-symptomatic stages, and late stages, in adults, children and pre-birth. Diagnosis typically includes the prognosis, the assessment of a predisposition or risk of development, the characterization of a subject to define most appropriate treatment (pharmaco-genetics), etc.

A particular object of this invention resides in a method of detecting the presence of or predisposition to drug-induced vestibular dysfunction, more particularly, GM-induced vestibular dysfunction in a subject, the method comprising (i) providing a sample from the subject and (ii) detecting the presence of an alteration in the NOS3 locus alone, or in the NOS3 locus, GSTP1 and GSTZ1 gene locus in combination, in said sample, the presence of said alteration is indicative of the presence of or predisposition to drug-induced vestibular dysfunction, more particularly, GM-induced vestibular dysfunction. Preferably, said alteration is a nucleotide substitution. More preferably, the invention concerns a method of detecting the presence of or predisposition to GM-induced vestibular dysfunction.

A particular object of this invention resides in a method of detecting the presence of or predisposition to drug-induced vestibular dysfunction, more particularly Gm-induced vestibular dysfunction, in a subject, the method comprising (i) providing a sample from the subject and (ii) detecting the presence of an alteration in the NOS3 mRNA alone, or in the NOS3, GSTP1 and GSTZ1 mRNA in said sample, the presence of said alteration is indicative of the presence of or predisposition to drug-induced vestibular dysfunction, more particularly GM-induced vestibular dysfunction. Preferably, said alteration is a nucleotide substitution. More preferably, the invention concerns a method of detecting the presence of or predisposition to GM-induced vestibular dysfunction.

An additional particular object of this invention resides in a method of detecting the presence or predisposition in a subject, the method comprising (i) providing a sample from the subject and (ii) detecting the presence of an alteration in the ENOS alone, or in ENOS, GST Pi, or GST Zeta 1 polypeptide in said sample, the presence of said alteration is indicative of the presence of or predisposition to drug-induced vestibular dysfunction, more particularly, GM-induced vestibular dysfunction. Preferably, said alteration is an amino acid substitution. More preferably, the invention concerns a method of detecting the presence of or predisposition to GM-induced vestibular dysfunction.

An other particular object of this invention resides in a method of assessing the response of a subject to treatment with aminoglycosides, more particularly GM, the method comprising (i) providing a sample from the subject and (ii) detecting the presence of an alteration in the NOS3 alone, or NOS3, GSTP1 and GSTZ1 gene locus, in the NOS3, GSTP1 and GSTZ1 mRNA or in the ENOS, GST Pi, or GST Zeta 1 polypeptide in said sample, the presence of said alteration is indicative of a particular response to said treatment. Preferably, said alteration is a nucleotide or amino acid substitution. More preferably, the invention concerns a method of assessing the response of a subject to treatment with GM.

An alteration in the gene may be any form of mutation(s), deletion(s), rearrangement(s) and/or insertions in the coding and/or non-coding region of the locus, alone or in various combination(s). Mutations more specifically include point mutations, as disclosed above. In a preferred embodiment of the present invention, the alteration is a nucleotide or amino acid substitution.

The detection of the presence of an altered NOS3, GSTP1 or GSTZ1 gene or an altered NOS3, GSTP1 or GSTZ1 mRNA sequence according to the present invention can be performed by sequencing all or part of the gene, polypeptide or RNA, by selective hybridization or by selective amplification, for instance.

A more specific embodiment comprises detecting the presence of a polymorphism in the NOS3, GSTP1 and GSTZ1 gene sequence or NOS3, GSTP1 and GSTZ1 mRNA of a subject. Preferably, the alteration detected in the NOS3, GSTP1 and GSTZ1 gene locus or NOS3, GSTP1 and GSTZ1 mRNA is selected from the group consisting of a guanine to thymine change at position 893 of the NOS3 gene, producing a glutamine to asparagine change at amino acid 298 of the translated protein ENOS, and/or a adenine to guanine change at position 312 of GSTP1 gene producing an isoleucine to valine change at amino acid 105 of the GST Pi protein and/or an adenine to guanine change at position 94 of the GSTZ1 gene producing a lysine to glutamine change at amino acid 32 of the GST Zeta 1 protein.

Altered RNA expression includes the presence of an altered RNA sequence, the presence of an altered RNA splicing or processing, the presence of an altered quantity of RNA, etc. These may be detected by various techniques known in the art, including by sequencing all or part of the RNA or by selective hybridization or selective amplification of all or part of said RNA, for instance.

Altered polypeptide expression includes the presence of an altered polypeptide sequence, the presence of an altered quantity of polypeptide, the presence of an altered tissue distribution, etc. These may be detected by various techniques known in the art, including by sequencing and/or binding to specific ligands (such as antibodies), for instance.

A further object of the present invention resides in a method of detecting the presence of or predisposition to drug-induced vestibular dysfunction, more particularly GM-induced vestibular dysfunction in a subject, the method comprising (i) providing a sample from the subject and (ii) detecting the presence of an altered ENOS, GST Pi, of GST Zeta 1 activity, the presence of said altered activity is indicative of the presence of or predisposition to drug-induced vestibular dysfunction, more particularly, GM-induced vestibular dysfunction.

As indicated above, various techniques known in the art may be used to detect or quantify altered gene or RNA expression or sequence, including sequencing, hybridization, amplification and/or binding to specific ligands (such as antibodies). Other suitable methods include allele-specific oligonucleotide (ASO), allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, heteroduplex analysis, RNase protection, chemical mismatch cleavage, ELISA, radio-immunoassays (RIA) and immuno-enzymatic assays (EEMA).

Some of these approaches (e.g., SSCA and CGGE) are based on a change in electrophoretic mobility of the nucleic acids, as a result of the presence of an altered sequence. According to these techniques, the altered sequence is visualized by a shift in mobility on gels. The fragments may then be sequenced to confirm the alteration.

Some others are based on specific hybridization between nucleic acids from the subject and a probe specific for wild-type or altered gene or RNA. The probe may be in suspension or immobilized on a substrate. The probe is typically labeled to facilitate detection of hybrids. By "specific hybridization" is intended a hybridization under stringent conditions.

Some of these approaches are particularly suited for assessing a polypeptide sequence or expression level, such as Northern blot, ELISA and RIA. These latter require the use of a ligand specific for the polypeptide, more preferably of a specific antibody.

Sequencing can be carried out using techniques well known in the art, using automatic sequencers. The sequencing may be performed on the complete gene or, more preferably, on specific domains thereof, typically those known or suspected to carry deleterious mutations or other alterations.

Amplification may be performed according to various techniques known in the art, such as by polymerase chain reaction (PCR), ligase chain reaction (LCR), strand displacement amplification (SDA) and nucleic acid sequence based amplification (NASBA). For example, a PCR method that may also be useful is Bi-PASA (Bidirectional PCR Amplification of Specific Alleles), as for example described in Liu et al. 1997, Genome Res. 7 389-399. Another potentially useful PCR method as allele-specification oligonucleotide hybridization, as for example described in Aitken et al., 1999, J Natl Cancer Inst 91 446-452.

It will also be well understood by the skilled person that identification of each polymorphism of the invention may be performed using any of a variety of techniques such as fluorescence-based melt curve analysis, SSCP analysis, denaturing gradient gel electrophoresis (DGGE) or direct sequencing of amplification products.

Melt curve analysis can be performed using fluorochrome-labeled allele-specific probes which form base-pair mismatches when annealing to wild-type DNA strands in heterozygotes. Alternatively, fluorescent DNA-intercalating dyes such as SYBR Green 1 can reveal the presence of these base-pair mismatches by virtue of their lower melting temperature ($T_m$) compared to fully complementary sequences. A useful example of allele-specific melt curve analysis can be found, for example, in International Publication No. WO97/46714.

DGGE also exploits $T_m$ differences, but uses differential electrophoretic migration through gradient gels as a means of distinguishing subtle nucleotide sequence differences between alleles. Examples of DGGE methods can be found in Fodde & Losekoot, 1994, Hum. Mutat. 3 83-9 and U.S. Pat. Nos. 5,045,450 and 5,190,856.

Each polymorphism used according to the invention may also be identified by direct sequencing of a PCR amplification product, for example. An example of nucleic acid sequencing technology is provided in Chapter 7 of CURRENT PROTOCOLS IN MOLECULAR BIOLOGY Eds. Ausubel et al. (John Wiley & Sons NY USA 1995-2001).

In yet another embodiment, mass spectroscopy (such as MALDI-TOF) may be used to identify nucleic acid polymorphisms according to mass. In a preferred form, such methods employ mass spectroscopic analysis of primer extension products, such as using the MassARRAY™ technology of Sequenom.

In a further embodiment, a polymorphism described herein linked to GM-induced vestibular dysfunction may be identified by a microarray method of the invention.

Microarray technology is well known in the art and examples of methods applicable to microarray technology are provided in Chapter 22 of CURRENT PROTOCOLS IN MOLECULAR BIOLOGY Eds. Ausubel et al. (John Wiley & Sons NY USA 1995-2001).

With respect to the present invention, a preferred microarray format comprises a substrate such as a glass slide or chip having an immobilized, ordered grid of a plurality of nucleic acid molecules, such as cDNA molecules, although without limitation thereto.

A microarray would typically comprise one or more nucleic acid having one or more gene polymorphism together with control nucleic acids.

Such a microarray could also include a plurality of other nucleic acids indicative of other diseases that have an underlying genetic basis and be useful in large scale genetic screening, for example. These techniques can be performed using commercially available reagents and protocols. Preferred techniques use allele-specific PCR or PCR-SSCP. Amplification usually requires the use of specific nucleic acid primers, to initiate the reaction.

In this regard, a particular object of this invention resides in a nucleic acid primer useful for amplifying sequences from the NOS3 gene, GSTP1 gene, and/or GSTZ1 gene or locus. Such primers are preferably complementary to, and hybridize specifically under stringent conditions to nucleic acid sequences in the gene locus. Particular primers are able to specifically hybridize under stringent conditions with a portion of the gene locus that flank a target region of said locus, said region comprising an alteration according to the present invention.

An aspect of this invention includes a pair of nucleic acid primers, wherein said pair comprises a sense and a reverse primers, and wherein said forward and a reverse primers (specified in SEQ ID NO:13 and 14, respectively, See Table S1 below) specifically amplify a NOS3 gene or RNA or a target region thereof, said region comprising an alteration according to the present invention, more particularly a substitution of the nucleotide G to T at position 893 in certain subjects having drug-induced vestibular dysfunction, more particularly, GM-induced vestibular dysfunction. In one embodiment, PCR-based restriction fragment length polymorphism analysis may be used. In this regard, the polymorphism in the NOS3 gene in the form of a G to T change at nucleotide 893, introduces a BanII restriction endonuclease site not ordinarily present at a corresponding position in a wild type gene.

In another aspect, this invention includes a pair of nucleic acid primers, wherein said pair comprises a sense and a reverse primers, and wherein said forward and a reverse primers (specified in SEQ ID NO:19 and 20, respectively. See Table S1 below) specifically amplify a GSTP1 gene or RNA or a target region thereof, said region comprising an alteration according to the present invention, more particularly a substitution of the nucleotide A to G at position 312 in certain subjects having drug-induced vestibular dysfunction, more particularly, GM-induced vestibular dysfunction. In one embodiment, PCR-based restriction fragment length polymorphism analysis may be used. In this regard, the polymorphism in the GSTP1 gene in the form of a A to G change at nucleotide 312, introduces a introduces a Alw26I cut site the G allele not ordinarily present at a corresponding position in a wild type gene.

In yet another aspect, this invention includes a pair of nucleic acid primers, wherein said pair comprises a sense and a reverse primers, and wherein said forward and a reverse primers (specified in SEQ ID NO:27 and 28, respectively. See Table S1 below) specifically amplify a GSTZ1 gene or RNA or a target region thereof, said region comprising an alteration according to the present invention, more particularly a substitution of the nucleotide A to G at position 94 in certain subjects having drug-induced vestibular dysfunction, more particularly, GM-induced vestibular dysfunction. In one embodiment, PCR-based restriction fragment length polymorphism analysis may be used. In this regard, the polymorphism at position 94 of GSTZ1 gene in the form of an A to G substitution introduces an Alw26I cut site not ordinarily present at a corresponding position in a wild type gene.

By using such primers, the detection of an amplification product indicates the presence of an alteration in the gene locus. In contrast, the absence of amplification product indicates that the specific alteration is not present in the sample. Typical primers of this invention are single-stranded nucleic acid molecules of about 5 to 60 nucleotides in length, more preferably of about 8 to about 25 nucleotides in length. The sequence can be derived directly from the sequence of the gene locus. Perfect complementarity is preferred, to ensure high specificity. However, certain mismatch may be tolerated.

gene locus in the sample. Also, various samples from various subjects may be treated in parallel.

A further particular object of this invention resides in a nucleic acid probe specific for a gene or RNA. Within the context of this invention, a probe refers to a polynucleotide sequence which is complementary to and capable of specific hybridization under stringent conditions with a (target portion of a) gene or RNA, and which is suitable for detecting

TABLE S1

Primers, annealing temperatures and enzymes used in the genotyping assays for each of the candidate polymorphisms.

| Gene | rs# | Forward Primer/SEQ ID NO: Reverse Primer/SEQ ID NO: | Temp (° C.) | Enzyme |
|---|---|---|---|---|
| MTRNR1 | nc1001807 | 5' GGGTCGAAGGTGGATTTAGC 3'/NO: 1<br>3' ACTCTGGTTCGTCCAAGTGC 5'/NO: 2 | 54 | BsmAI |
| MYO6 | rs13211391 | 5' GGGAGCAAGCTTTATTCGTT 3'/NO: 3<br>3' CTATGTTGCCCAGGCTGACT 5'/NO: 4 | 49 | SspI |
| MYO7A | rs948962 | 5' TCTTTCCTGAGAAGGAGCAG 3'/NO: 5<br>3' ATGGGCCGAGCTTTCTTTAT 5'/NO: 6 | 57 | EcoO109I |
|  | rs1052030 | 5' CTTCTCTTCCCCCTTGTGTG 3'/NO: 7<br>3' CAGAGTCGCAGAGCTTCACC 5'/NO: 8 | 51 | DpnII |
| MYO15 | rs854777 | 5' CACTCCCCAACCTGACATCT 3'/NO: 9<br>3' GCTCAGCTCCTAGAGGGACA 5'/NO: 10 | 57 | SfoI |
| BDNF | rs6265 | 5' GAGGCTTGACATCATTGGCT 3'/NO: 11<br>3' CGTGTACAAGTCTGCGTCCT 5'/NO: 12 | 60 | Eco72I |
| NOS3 (ENOS) | rs1799983 | 5' GACCCTGGAGATGAAGGCAGGAG 3'/NO: 13<br>3' ACCTCCAGGATGTTCTAGCGGTGA 5'/NO: 14 | 60 | BanII |
|  | rs10952298 | 5' CCAGGCCCACCCCAACCTTAT 3'/NO: 15<br>3' TCATTCAGTGACGCACGCTT 5'/NO: 16 | 53 | MspI |
|  | Intron 4 VNTR | 5' CCTGGTTATCAGGCCCTATG 3'/NO: 17<br>3' AGGCTGCTCCTGCTACTGAC 5'/NO: 18 | 59 | N/A |
| GSTP1 | rs1695 | 5' CTCTATGGGAAGGACCAGCAGGA 3'/NO: 19<br>3' CAAGCCACCTGAGGGGTAAGG 5'/NO: 20 | 65 | Alw26I |
|  | rs1138272 | 5' TTGACAGGATTTGGTACTAGCC 3'/NO: 21<br>3' TGGTCTCCCACAATGAAGGT 5'/NO: 22 | 52 | AciI |
| GSTM3 | rs1799735 | 5' CCTCAGTACTTGGAAGAGCT 3'/NO: 23<br>3' CACATGAAAGCCTTCAGGTT 5'/NO: 24 | 52 | MnlI |
| GSTZ1 | rs7972 | 5' TGACCACCCAGAAGTGGTAG 3'/NO: 25<br>3' AGTCCACAAGACACAGGTTC 5'/NO: 26 | 52 | FokI |
|  | rs3177427 | 5' TGACCACCCAGAAGTGGTAG 3'/NO: 27<br>3' AGTCCACAAGACACAGGTTC 5'/NO: 28 | 52 | Alw26I |

A particular detection technique involves the use of a nucleic acid probe specific for wild-type or altered gene or RNA, followed by the detection of the presence of a hybrid. The probe may be in suspension or immobilized on a substrate or support (as in nucleic acid array or chips technologies). The probe is typically labeled to facilitate detection of hybrids.

In this regard, a particular embodiment of this invention comprises contacting the sample from the subject with a nucleic acid probe specific for an altered gene locus, and assessing the formation of an hybrid. In a particular, preferred embodiment, the method comprises contacting simultaneously the sample with a set of probes that are specific, respectively, for wild type gene locus and for various altered forms thereof. In this embodiment, it is possible to detect directly the presence of various forms of alterations in the polynucleotide polymorphisms, preferably the polymorphism associated with NOS3, GSTP1, or GSTZ1 alleles which predispose to or are associated with GM-induced vestibular dysfunction. Probes are preferably perfectly complementary to the gene, RNA, or target portion thereof. Probes typically comprise single-stranded nucleic acids of between 8 to 1000 nucleotides in length, for instance of between 10 and 800, more preferably of between 15 and 700, typically of between 20 and 500. It should be understood that longer probes may be used as well. A preferred probe of this invention is a single stranded nucleic acid molecule of between 8 to 500 nucleotides in length, which can specifically hybridize under stringent conditions to a region of a gene or RNA that carries an alteration.

A specific embodiment of this invention is a nucleic acid probe specific for an altered (e.g., a mutated) gene or RNA, i.e., a nucleic acid probe that specifically hybridizes under stringent conditions to said altered NOS3, GSTP1, or GSTZ1 gene or RNA and essentially does not hybridize under stringent conditions to a gene or RNA lacking said alteration. Specificity indicates that hybridization to the target sequence generates a specific signal which can be distinguished from the signal generated through non-specific hybridization. Perfectly complementary sequences are preferred to design probes according to this invention. It should be understood, however, that certain mismatch may be tolerated, as long as the specific signal may be distinguished from non-specific hybridization.

The sequence of the probes can be derived from the sequences of the gene and RNA as provided in the present application. Nucleotide substitutions may be performed, as well as chemical modifications of the probe. Such chemical modifications may be accomplished to increase the stability of hybrids (e.g., intercalating groups) or to label the probe. Typical examples of labels include, without limitation, radioactivity, fluorescence, luminescence, enzymatic labeling, etc.

As indicated above, alteration in the gene locus may also be detected by screening for alteration(s) in polypeptide sequence or expression levels. In this regard, a specific embodiment of this invention comprises contacting the sample with a ligand specific for an altered polypeptide and determining the formation of a complex.

Different types of ligands may be used, such as specific antibodies. In a specific embodiment, the sample is contacted with an antibody specific for an altered polypeptide and the formation of an immune complex is determined. Various methods for detecting an immune complex can be used, such as ELISA, radio-immunoassays (RIA) and immuno-enzymatic assays (IEMA).

In a specific embodiment, the method comprises contacting a sample from the subject with (a support coated with) an antibody specific for an altered form of a polypeptide, and determining the presence of an immune complex. In a particular embodiment, the sample may be contacted simultaneously, or in parallel, or sequentially, with various (supports coated with) antibodies specific for different forms of a polypeptide, such as a wild-type and various altered forms thereof.

The invention also relates to a diagnostic kit comprising products and reagents for detecting in a sample from a subject the presence of an alteration in the gene or in the protein, in the RNA or protein expression and/or in protein activity of any of the following genes and proteins, NOS3 gene and ENOS protein, in the GSTP1 gene or protein, in the GSTZ1 gene or protein. Said diagnostic kit according to the present invention comprises any primer, any pair of primers, any nucleic acid probe and/or any antibody described in the present invention. Said diagnostic kit according to the present invention can further comprise reagents and/or protocols for performing a hybridization, amplification or antigen-antibody immune reaction.

Notwithstanding the foregoing, the invention contemplates other nucleic acid detection methods that may be useful for detecting the gene polymorphisms described herein.

It will be appreciated from the foregoing that the invention contemplates a kit for molecular genetic detection of a predisposition to GM-induced vestibular dysfunction. In a particular embodiment, the kit comprises
(a) primers for nucleic acid sequence amplification of at least a fragment containing a polymorphism of NOS3; and/or
(b) primers for nucleic acid sequence amplification of at least a fragment containing a polymorphism of GSTP1; and/or
(c) primers for nucleic acid sequence amplification of at least a fragment containing a polymorphism of GSTZ1.

The kit may further comprise a corresponding restriction endonuclease which digests the fragment containing the polymorphism. One or more other reagents are contemplated such as probes for hybridization-based methods and detection reagents useful in enzymatic/colorimetric detection of nucleic acids, although without limitation thereto.

All publications, including, but not limited to patents and patent applications, cited in this specification are herein incorporated by reference as if each individual publication were specifically and individually indicated to be incorporated by reference herein as though fully set forth.

The invention is further described in detail to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided therein.

The following Materials and Methods were used in lyophilization experiments, the results of which are found in the Brief Description of the Drawings above.

Materials and Methods

Subjects: Subjects were recruited for participation in a case/control study. Cases were recruited from various vestibular dysfunction support groups through advertisements and direct mailings. Cases were included if they could document profound unilateral or bilateral vestibular loss due specifically to GM administration after the age of 18 yr. Approximately age-matched control subjects were included if they did not have vestibular dysfunction, with or without previous GM therapy. Normal vestibular function was determined with the use of a clinical balance function questionnaire and medical history information. There are no apparent sex or racial differences in susceptibility to GM-induced vestibular dysfunction, so no inclusion limitations were made on those parameters, although the vast majority of recruited subjects were white. Because allele frequencies for many polymorphisms differ by race and only 10 non-white subjects completed the study, all results are presented for the 263 white participants. Children have higher risk for GM-induced ototoxicity, so only individuals >18 yr. and who were >18 yr. at the time of GM therapy were included. All subjects provided written informed consent and all procedures were approved by the University of Maryland Institutional Review Board.

Procedures: Potential subjects completed medical history and balance function questionnaires, and patients specifically provided medical record release authorizations. The questionnaires addressed the date of GM therapy (age of administration), reason for GM therapy, onset of vestibular symptoms following GM therapy, changes in vestibular function over time, and family history of vestibular dysfunction regardless of origin. Vestibular loss was confirmed through medical records obtained from each patient's physician, particularly focusing on vestibulo-ocular reflex (VOR) gains less than 3 standard deviations below the mean and abnormal phase and time constants in pseudorandom sum of sines rotation from 0.01-1.5 Hz., or electronystagmographic verification of absent responses to caloric irrigation. GM must have been indicated as the most likely cause of the vestibular dysfunction, according to the medical records, for inclusion in the study. Controls completed a similar medical history questionnaire and were specifically asked about GM administration.

TABLE 1

Candidate genes selected for genotyping, including gene symbol, chromosome position, polymorphisms genotyped, and the corresponding reference SNP numbers.

| Name | Symbol | Location | Reference Sequence | Polymorphism (nucleotide) | Polymorphism (amino acid) | rs# |
|---|---|---|---|---|---|---|
| Mitochondrially encoded 12S RNA | MT-RNR1 | Mito. | NC_001807.4 | m.1555A > G | | — |
| Myosin VI | MYO6 | 6q13 | NM_004999.3 | c.2417-87A > C | | rs13211391 |
| Myosin VIIA | MYO7A | 11q13 | NM_000260.2 | c.46C > T c.5859A > C | p.Ser16Leu p.Ile1954Leu | rs1052030 rs948962 |
| Myosin XVA | MYO15A | 8q24 | NM_016239.2 | c.5928C > T | p.Arg1977Lys | rs854777 |
| BDNF | BDNF | 11p13 | NM_001709.3 | c.195A > G | p.Val66Met | rs6265 |
| Nitric oxide synthase 3 (ENOS) | NOS3 | 7q36 | NM_000603.3 | c.893G > T c.-813T > C* c.582 + 250N$_{27}$(4_5)** | p.Glu298Asp | rs1799983 rs2070744 — |
| GST Pi | GSTP1 | 11q13 | NM_000852.2 | c.312A > G c.340C > T | p.Ile105Val p.Ala114Val | rs1695 rs1138272 |
| GST M3 | GSTM3 | 1p13 | NM_000849.3 | c.468 + 21_22insAGG | | rs1799735 |
| GST Zeta 1 | GSTZ1 | 14q24 | NM_145870.1 | c.94A > G c.124A > G | p.Lys32Glu p.Arg42Gly | rs3177427 rs7972 |

SNP, single nucleotide polymorphism; BDNF, brain-derived neurotrophic factor; ENOS; endothelial nitric oxide synthase; GST, glutathione S-transferase; InDel, insertion/deletion polymorphism.
*often referred to as T-786C.
**often referred to as the intron 4 variable nucleotide tandem repeat.

Genotyping: DNA was collected using the Epicentre BuccalAmp DNA Extraction Kit, which relies on buccal swabs. Extraction was performed following the manufacturer's instructions and DNA was refrigerated. When extractions failed, new DNA samples were collected where possible and the extraction was repeated. All subjects were genotyped for the candidate polymorphisms shown in Table 1, with genotyping performed randomly on case and control samples and blinded to group status. Restriction-digest and gel electrophoresis methods were used for all polymorphisms, relying either on previously published methods or on de novo designs. Primers, annealing temperatures and specific enzymes are provided in the supplementary material (Table S1). Multiple sequence-verified control samples were used in all genotyping assays to verify accuracy of the genotyping results. Uncertain genotypes were repeated with sequence verified control samples. Sequence confirmation was performed for 20 samples across all polymorphisms with 99% consistency.

Statistics: T-tests and chi square tests were performed to compare demographic and clinical measurements between cases and controls using SAS software. Allele frequency differences were compared between cases and controls, using the software PowerMarker (www.powermarker.net; (Zaykin et al., 2002, Hum. Hered. 53, 79-91). Hardy-Weinberg equilibrium (HWE) was tested in both cases and controls using Powermarker and the inbreeding coefficients were calculated for the two groups independently. In addition, the Armitage trend test was used to compare genotype distributions between cases and controls as this test is not dependent on assumptions about HWE (Sasieni, P. D. 1997, Biometrics 53, 1253-1261). Haplotype frequencies in cases and controls were also estimated with PowerMarker. The haplotype trend analysis in Power Marker was performed to test for haplotype frequency differences between cases and controls. The relative effects of specific haplotypes were tested using the estimated haplotype frequencies from PowerMarker and calculating the number of chromosomes of each type and comparing their distributions relative to all other haplotypes in cases and controls. An odds ratio was calculated using the generated 2×2 tables using SAS. As this was the first analysis of these genes for vestibular ototoxicity susceptibility, correction for multiple testing was not performed; however, all analyses that were performed are presented in the results section. Multilocus analysis was performed using the multifactor dimensionality reduction (MDR) method (Ritchie et al., 2001, Am. J. Hum. Genet. 69, 138-147). Briefly, MDR is nonparametric and model free, making it a unique tool for identifying gene x gene interactions. MDR collapses all of the genetic data into two categories, high and low risk, by comparing all single locus and all multilocus combinations and then categorizing each genotype into either high risk or low risk on the basis of the ratio of cases to controls who have that genotype. MDR ultimately selects one genetic model, either single or multilocus, that most successfully predicts phenotype or disease status. The prediction error of the model is estimated using 10-fold cross validation. The 10-fold cross validation is repeated 10 times to ensure that results are not due to chance divisions of the data. The average number of times that the same best model comes up is given as the cross-validation consistency and is represented as a continuous value from 1-10. Cross validation consistency and prediction error minimization are both used to choose the single best model. Statistical significance is determined empirically by permuting the case and control labels 1,000 times. Generating the p values using permutations eliminates the problem of multiple testing.

Multilocus models generated by MDR were subjected to dendrogram analysis as described by Moore et al. (Moore et al., 2006, J. Theor. Biol. 241, 252-261). The dendrograms allow visualization of the nature of the interactions between variables and to assess the statistical nature of the relationship between markers (i.e., redundant, additive, or synergistic). The determination of the nature of the interactions is based on the information gain associated with variable (genotype) interactions, using the algorithm of Jakulin and colleagues (Jakulin et al., 2003, Lect. Notes Artif. Intell. 2780, 229-238), as implemented in Moore et al. (supra). Interaction dendrograms were created using the MDR software.

Example 1

A total of 383 subjects were initially recruited for the study, with 273 subjects successfully matching all inclusion criteria. Of the 110 excluded subjects, 45 were excluded due to lack of qualifying evidence of GM-induced ototoxicity, while all other subjects failed to complete various aspects of the study. Subject characteristics for the 263 white subjects are shown in Table 2. More women than men were recruited for both the case and control groups, and the cases (both men and women) were significantly older than controls. Cases had significantly higher rates of hearing and renal complications, which were attributed to their GM therapy.

Analysis of genotype frequencies for deviations from HWE was performed independently in cases and controls. In cases, 4 of the 15 SNPs deviated from HWE (GSTP1 p.Ala114Val, GSTZ1 p.Lys32Glu, MTRNR1 m.1555A>G, MYO7A p.Ser16Leu) with p values between 0.001 and 0.046. In controls 6 of the 15 SNPs deviated from HWE (GSTM3 c.468+21_22insAGG, GSTP1 p.Ala114Val, GSTZ1 p.Lys32Glu, NOS3 p.Glu298Asp, MYO7A p.Ser16Leu, MYO6 c.2417-87A>C) with p values ranging from 0.001 to 0.013) with the exception of GSTZ1 p.Lys32Glu with p<0.0001. Repeat genotyping of these SNPs was performed in the entire sample and showed 97% replication.

TABLE 2

Subject characteristics.

|  | Cases | Controls |
|---|---|---|
| N men, N women | 55, 82 | 54, 72 |
| Age, yr. (SD) | 61.4 (12.7) | 56.1 (13.4)* |
| Age of GM admin, yr. (SD) | 55.9 (12.9) | NA** |
| N Unilateral, N Bilateral | 70, 67 | NA |
| Hearing complications[a], N (%) | 47 (34%) | 4 (3%)* |
| Renal complications, N (%) | 20 (14%) | 0* |
| Family history of vertigo, N (%) | 20 (15%) | 11 (9%) |
| Family history of balance problems, N (%) | 12 (9%) | 16 (13%) |

*P < 0.05 vs. cases.
**Two controls received GM therapy.
[a]Does not distinguish between hearing loss, tinnitus, or other GM-related hearing complications.

Statistical analysis first proceeded by examining each polymorphism individually in relation to case/control status. The first set of analyses examined allele frequency with GM-induced vestibular dysfunction and revealed three genes significantly associated (NOS3 p.Glu298Asp, p=0.03; GSTZ1 p.Arg42Gly, p=0.02; GSTM3 c.468+21_22insAGG, p=0.03). Analysis of genotype frequency with the Armitage trend test revealed that the NOS3 p.Glu298Asp polymorphism was significantly associated with GM-induced vestibular dysfunction (p=0.03) as was GSTZ1 p.Arg42Gly (p=0.03). GSTM3 was marginally significant for the trend test (p=0.055). The minor allele frequency for NOS3 p.Glu298Asp (Asp allele) was 37% in cases compared to 27% in controls.

Haplotype analyses were performed for polymorphisms within particular genes or biological systems (i.e., a pseudo-haplotype across related genes). The pseudo-haplotype analysis was used to determine whether inherited variants in different genes that may have similar or related functions cluster differently in cases vs. controls. For the three polymorphisms within the NOS3 gene, no haplotype association was identified (p=0.51). Similarly, a pseudo-haplotype analysis of all polymorphisms within the myosin genes did not reveal a significant association (p=0.31). Pseudo-haplotype analysis of the five polymorphisms across all glutathione S-transferase (GST) genes revealed a significant association (p=0.002). Across the 9 pseudo-haplotypes identified as being present in at least 5% of cases or controls, three haplotypes (G-G-A-A-T (SEQ ID NO:29), G-A-A-G-C (SEQ ID NO:30) and A-A-A-A-C (SEQ ID NO:31) were significantly more prevalent in cases compared to controls (all p≦0.012; data not shown).

Figure 2:
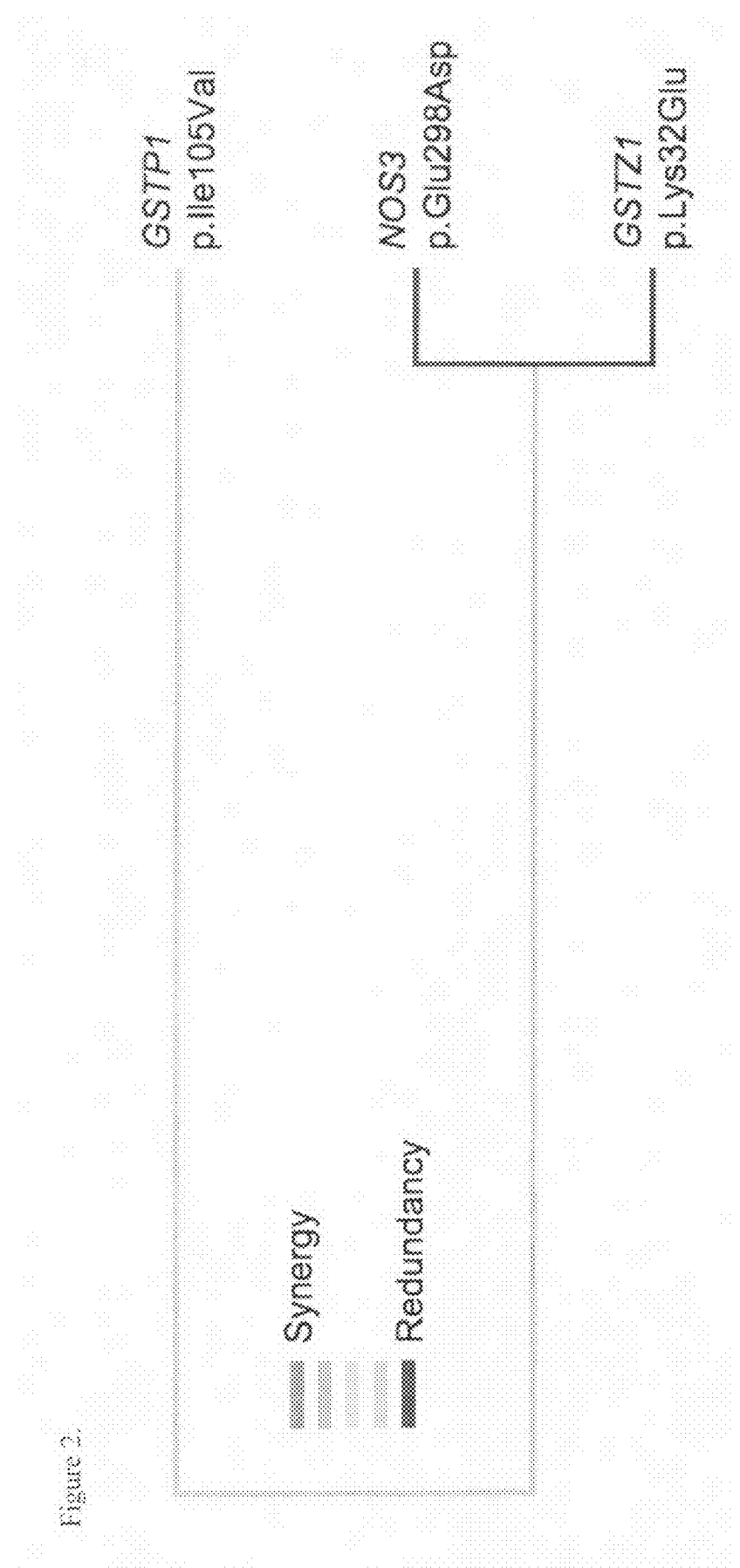
FIG. 2. Interaction dendrogram showing strong redundancy between GSTZ1 p.Lys32Glu and NOS3 p.Glu298Asp, with a synergistic or additive interaction with GSTP1 p.Ile105Val, consistent with the best fitting 3-locus MDR model. The nature of the interaction is depicted in the legend.

Finally, MDR analysis was performed across all 15 polymorphisms in the nine candidate genes. The best model for each number of variants is shown in Table 3. Similar to the single-gene analysis, the single-gene MDR model with highest prediction accuracy (57%; p=0.011) consisted of the NOS3 p.Glu298Asp polymorphism. Across all of the MDR models (containing up to 5 loci), the most accurate predictor was the three-genotype model that included NOS3 p.Glu298Asp, GSTZ1 p.Lys32Glu, and GSTP1 p.Ile105Val, which predicted case/control status with 64% accuracy (p=0.009). As shown in FIG. 1, specific allelic combinations of these three polymorphisms were identified as high and low risk (dark shading indicates higher risk). In particular, combinations including NOS3 p.Glu298Asp Glu-allele (G) homozygotes tended to have the lowest risk. FIG. 2 shows a dendrogram of the interaction analysis of the 3-locus model, which shows a strong synergistic interaction between NOS3 p.Glu298Asp and GSTZ1 p.Lys32Glu, while GSTP1 p.Ile105Val appears to have an additive effect with the other two polymorphisms.

DISCUSSION

The present study is the first to report susceptibility genes for gentamicin-induced vestibular dysfunction. The NOS3 (ENOS) p.Glu298Asp polymorphism (Asp allele) was independently associated with risk for GM-induced vestibular dysfunction, while the three-gene combination of NOS3 (p.Glu298Asp), GSTZ1 (p.Lys32Glu), and GSTP1 (p.Ile105Val) had 64% accuracy in distinguishing cases from controls. While additional work will be needed to verify these results, the importance of these genes to oxidative stress, known to be a key factor in the mechanism of GM-induced hair cell damage, make them important contributors toward a potential screening tool useful for limiting the occurrence of GM-induced vestibular dysfunction (Bitner-Glindzicz et al., 2007, BMJ 335, 784-785).

TABLE 3

MDR models, showing prediction accuracy and cross-validation consistency (CVC) performed as measured by the number of times out of 10 subdivisions of the data the same loci appear in the model.

| Model | Loci | | Accuracy | CVC |
|---|---|---|---|---|
| 1 locus | NOS3 p.Glu298Asp | | 0.57 | 10 |
| 2 locus | NOS3 p.Glu298Asp | GSTP1 p.Ile105Val | 0.55 | 5 |

TABLE 3-continued

MDR models, showing prediction accuracy and cross-validation consistency
(CVC) performed as measured by the number of times out of 10 subdivisions
of the data the same loci appear in the model.

| Model | Loci | | | | | Accuracy | CVC |
|---|---|---|---|---|---|---|---|
| 3 locus | NOS3 p.Glu298Asp | GSTP1 p.Ile105Val | GSTZ1 p.Lys32Glu | | | 0.64 | 10 |
| 4 locus | NOS3 p.Glu298Asp | GSTP1 p.Ile105Val | GSTZ1 p.Lys32Glu | GSTZ1 p.Arg42Gly | | 0.52 | 2 |
| 5 locus | NOS3 p.Glu298Asp | GSTP1 p.Ile105Val | GSTZ1 p.Lys32Glu | GSTZ1 p.Arg42Gly | BDNF p.Val66Met | 0.63 | 8 |

In the present study, we have focused specifically on GM because of its particularly high vestibulotoxicity, common use, and the fact that GM is not metabolized, but simply excreted by the kidney (Begg and Barclay, 1995, Br. J. Clin. Pharmacol. 39, 597-603), so any genetic influence on GM-related ototoxicity is hypothesized to occur at the level of the vestibular system specifically. As outlined above, NO and related ROS are important for the onset of hair cell degradation in response to GM-related compounds. Aminoglycosides are proposed to influence mitochondrial protein synthesis, resulting in NO and ROS generation and JNK activation, which then leads to apoptosis of hair cells and degradation of inner ear function (Ylikoski et al., 2002, Hearing Res. 163, 71-81). Both scavenging of ROS and blockade of NO production have been shown to reduce ototoxic damage resulting from aminoglycosides (Takumida and Anniko, 2002, Acta Otolaryngol. 122, 10-15; Takumida and Anniko, 2005, ORL J. Otorhinolaryngol Relat. Spec. 67, 276-281; Takumida et al., 2003, Acta Otolaryngol 123, 8-13; Takumida et al., 1999, ORL J. Otorhinolaryngol. Relat. Spc. 61, 63-70; Watannabe et al., 2000, Anti-Canc. Drugs 11, 731-735; Wittke-Thompson et al., 2005, Am. J. Hum. Genet. 76, 967-986). In the present study, missense polymorphisms in three genes, NOS3, GSTZ1, and GSTP1 were associated with GM-induced vestibular dysfunction; all three genes are related to NO production and ROS inactivation.

The NOS3 p.Glu298Asp polymorphism has been shown to be related to NO production, with the 298Asp allele having lower levels of NO production in several studies (Sofowora et al., 2001, Pharmacogenetics 11, 809-814; Tanus-Santos et al., 2002, Pharmacogenetics 12, 407-413; Veldman et al., 2002, J. Hypertens. 20, 2023-2027). Our data are not consistent with these previous findings in that we observed a higher proportion of 298Asp alleles in cases compared to controls; higher NO levels associated with ototoxicity would be expected of the 298Glu allele rather than the Asp allele. One possible explanation is that the p.Glu298Asp polymorphism is acting as a marker for other variants within the NOS3 gene region. Dendrogram analyses performed within the present study for 4-locus models were consistent with this, as the analyses showed a synergistic interaction between the NOS3 p.Glu298Asp and c.-813T>C (also known as T-786C) polymorphisms (data not shown). This can be better understood when these two NOS3 variants are combined as a new composite variable in an MDR analysis as discussed by Moore et al. (2006, J. Theor. Biol. 241, 252-261). When the data were analyzed this way for the present study, the constructed variable (p.Glu298Asp+c.-813T>C) was the best single variable predictor, with almost the same accuracy as the three-locus MDR model presented in Table 3 (analyses not shown). Previous studies have shown significant linkage disequilibrium between these two NOS3 polymorphisms (Colombo et al., 2003, Clin. Chem. 49, 389-395; Hassan et al., 2004, Stroke 35, 654-659) in addition to a third intron 4 tandem repeat polymorphism (Hassan et al., 2004, supra; Karasneh et al., 2005, Rheumatology 44, 614-617). In fact, Hassan et al. (2004, supra) showed no influence of the p.Glu298Asp polymorphism alone on plasma NO levels, but haplotypes encompassing the c.-813T>C and intron 4 [c.582+250N$_{27}$(4_5)] variants were related to NO levels. Thus, additional work is necessary to clarify the direct or indirect role of the p.Glu298Asp variant in NOS3 in GM-induced vestibular ototoxicity susceptibility in relation to the full haplotype structure of this gene region. The glutathione S-transferase (GST) supergene family encodes a number of enzymes that catalyze the detoxification of various cytotoxic drugs and protect against DNA damage, possibly through direct ROS inactivation (Hayes et al., 2000, Pharmacology 61, 154-166). In fact, the activity of GST Pi, an endogenous inhibitor of JNK, has been shown to correlate with ototoxic sensitivity (Whitlon et al., 1999, Hearing Res. 137, 43-50). Ylikoski et al. (2002, supra) postulate that JNK activation is the critical step to hair cell degradation in response to ototoxic drugs, so the activity of GSTs, especially GST Pi, would be predicted to influence hair cell apoptosis. In the present study, both GSTZ1 p.Lys32Glu and GSTP1 p.Ile105Val were present in the final three-gene MDR predictive model, and both of these polymorphisms have been shown to be functional (Blackburn et al., 2000, Pharmacogenetics 10, 49-57; Watson et al., 1998, Carcinogenesis 19, 275-280; Zhong et al., 2006, Eur. J. Pharm. Sci. 28, 77-85). Specifically, the GSTZ1 p.Lys32Glu has been shown to affect enzyme activity in combination with the nearby Arg42Gly variant (Blackburn et al., 2000, supra) and the GSTP1 105Val allele has been associated with lower enzyme activity (Watson et al., 1998, supra; Zhong et al., 2006, supra). Though the p.Arg42Gly polymorphism was not present in the final three-gene MDR model, it was present in the four- and five-locus MDR models and in the single gene allele association analyses. How these specific polymorphisms interact to increase susceptibility to GM-induced ototoxicity cannot be determined from the present study, though the MDR analysis suggests that interactions among the genes are important. Several of the candidate genes selected for the present study did not demonstrate a significant association, either individually or in combination with other genes. For example, none of the myosin genes were found to be associated, despite their apparent importance to hair cell structure and function (Watson et al., 1998, supra). Similarly, although the mitochondrially encoded 12S RNA (MTRNR1) gene has been associated with aminoglycoside-induced hearing loss (Fischel-Ghodsian et al., 1999, Ann. N.Y. Acad. Sci. 884, 99-109), that gene was not associated with GM-induced vestibular dysfunction in the current study or in a previous investigation (Braverman et al., 1996, Arch. Otolaryngol. Head Neck Surg. 122, 1001-1004). Because several studies now indicate different susceptibilities for GM-induced hearing loss compared to GM-induced vestibulotoxicity, this result is not unexpected.

Finally, BDNF limits ototoxic damage when provided simultaneously with GM (Lopez et al., 1999, Am. J. Otol. 20, 317-324) and reduced GM-related ototoxicity has been demonstrated with the combination of a NOS inhibitor with BDNF (Takumida and Anniko, 2002, supra; Takumida et al., 2003, supra); however, BDNF genotype was not associated with GM-induced vestibulotoxicity in the present study. That said, BDNF was present in the five-locus MDR model and had a tendency toward significance in the Armitage trend test (p=0.09), so the possibility that BDNF acts as a modifying factor cannot be completely discounted.

The basis for the deviation from HWE in some of the polymorphisms is unclear. While we cannot completely eliminate the possibility of genotyping error, all quality control measures used in the present study demonstrated accurate and replicable genotype data. In addition, the fact that the direction of deviation from HWE differed in cases (inbreeding coefficient f=−0.11) and controls (inbreeding coefficient f=0.28) for one of the significant single locus associations (NOS3 p.Glu298Asp) further supports the conclusion that the deviations were unlikely to be from genotyping error. As shown by Wittke-Thompson et al. (2005, supra) inbreeding coefficients in opposite directions are indicative of genetic association, and it is unlikely for the sign of the inbreeding coefficients to be opposite in cases and controls if genotyping analyses were done without respect to phenotype. In contrast, the GSTZ1 p.Lys32Glu analysis does not necessarily fit expected patterns of true association based on the pattern of deviations from HWE (Wittke-Thompson et al., 2005, supra) suggesting caution in interpreting the findings for this variant.

As emphasized previously, these results will require additional validation in an independent sample; however, the totality of the evidence provides considerable rationale for continued study of NOS3 as a susceptibility gene for GM-induced vestibulotoxicity, possibly in combination with GST genes.

The present study is not without limitations. Within the questionnaire data, dosages of GM were not known for the vast majority of subjects, so that information could not be included in the analysis. The population-based control sample was generally not exposed to gentamicin, which would have provided the most powerful contrast to the cases. Thus, a small number of individuals in the control population is expected to be susceptible; however, the inclusion of a small number of susceptible controls results in a reduction of power making the study design and results more conservative. Population structure, which was not tested in the present study, represents a possible limitation, though it is unlikely based on recent data from an extensive study performed in >16,000 individuals of heterogeneous European descent (T.W.T.C.C. Consortium, 2007, Genome-wide association study of 14,000 cases of seven common diseases and 3,000 shared controls, Nature 447, 661-678). The results showed that only a small fraction (n=13) of >465,000 polymorphisms demonstrated evidence of strong geographical variation, and the authors concluded that populations structure was minimal in the population (T.W.T.C.C. Consortium, 2007, supra). Finally, we recognize that other candidate genes could be envisioned for this study. Nonetheless, we focused our initial candidate gene list on what we viewed as the most important targets of investigation and have identified an important combination of genes predicting 64% of responses to GM with respect to vestibular dysfunction from which more sophisticated future investigations can be initiated.

What is claimed is:

1. A kit comprising: (i) a NOS3 primer pair consisting of a first primer consisting of SEQ ID NO: 13 and a second primer consisting of SEQ ID NO: 14; (ii) a GSTP1 primer pair consisting of a first primer consisting of SEQ ID NO: 19 and a second primer consisting of SEQ ID NO: 20; and (iii) a GSTZ1 primer pair consisting of a first primer consisting of SEQ ID NO: 27 and a second primer consisting of SEQ ID NO: 28.

2. A kit for determining if a human subject has an increased susceptibility to gentamicin-induced vestibular dysfunction comprising: (i) a NOS3 primer pair consisting of a first primer consisting of SEQ ID NO: 13 and a second primer consisting of SEQ ID NO: 14; (ii) a GSTP1 primer pair consisting of a first primer consisting of SEQ ID NO: 19 and a second primer consisting of SEQ ID NO: 20; and (iii) a GSTZ1 primer pair consisting of a first primer consisting of SEQ ID NO: 27 and a second primer consisting of SEQ ID NO: 28.

3. A method for determining if a human subject has an increased susceptibility to gentamicin-induced vestibular dysfunction comprising:
obtaining a biological sample from a human subject comprising NOS3, GSTP1 and GSTZ1 nucleic acids;
amplifying the NOS3, GSTP1 and GSTZ1 nucleic acids present in the biological sample to produce NOS3, GSTP1 and GSTZ1 amplification products, wherein the amplifying is performed using (i) a NOS3 primer pair consisting of a first primer consisting of SEQ ID NO: 13 and a second primer consisting of SEQ ID NO: 14; (ii) a GSTP1 primer pair consisting of a first primer consisting of SEQ ID NO: 19 and a second primer consisting of SEQ ID NO: 20; and (iii) a GSTZ1 primer pair consisting of a first primer consisting of SEQ ID NO: 27 and a second primer consisting of SEQ ID NO: 28; and analyzing the NOS3, GSTP1 and GSTZ1 amplification products to detect the presence or absence of a NOS3 c.893G>T polymorphism, a GSTP1 c.312A>G polymorphism, and a GSTZ1 c.94A>G polymorphism, wherein the presence of each of the NOS3 c.893G>T, GSTP1 c.312A>G, and GSTZ1 c.94A>G polymorphisms indicates that the human subject has an increased susceptibility to gentamicin-induced vestibular dysfunction.

4. A method for determining if a human subject has an increased susceptibility to gentamicin-induced vestibular dysfunction comprising:

obtaining a biological sample from a human subject comprising NOS3, GSTP1 and GSTZ1 nucleic acids; and analyzing the NOS3, GSTP1 and GSTZ1 nucleic acids present in the biological sample to detect the presence or absence of a NOS3 c.893G>T polymorphism, a GSTP1 c.312A>G polymorphism, and a GSTZ1 c.94A>G polymorphism, wherein the presence of each of the NOS3 c.893G>T, GSTP1 c.312A>G, and GSTZ1 c.94A>G polymorphisms indicates that the human subject has an increased susceptibility to gentamicin-induced vestibular dysfunction.

* * * * *

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial sequence
<220> FEATURE:
<223> OTHER INFORMATION: MTRNR1 forward primer

<400> SEQUENCE: 1
gggtcgaagg tggatttagc                                            20

<210> SEQ ID NO 2
<211> LENGTH: 20
<212> TYPE: DNA
<213> ORGANISM: Artificial sequence
<220> FEATURE:
<223> OTHER INFORMATION: MTRNR1 reverse primer

<400> SEQUENCE: 2
actctggttc gtccaagtgc                                            20

<210> SEQ ID NO 3
<211> LENGTH: 20
<212> TYPE: DNA
<213> ORGANISM: Artificial sequence
<220> FEATURE:
<223> OTHER INFORMATION: MYO6 forward primer

<400> SEQUENCE: 3
```

-continued gggagcaagc tttattcgtt                                           20

<210> SEQ ID NO 4
<211> LENGTH: 20
<212> TYPE: DNA
<213> ORGANISM: Artificial sequence
<220> FEATURE:
<223> OTHER INFORMATION: MY06 reverse primer

<400> SEQUENCE: 4
ctatgttgcc caggctgact                                           20

<210> SEQ ID NO 5
<211> LENGTH: 20
<212> TYPE: DNA
<213> ORGANISM: Artificial sequence
<220> FEATURE:
<223> OTHER INFORMATION: MY07A forward primer

<400> SEQUENCE: 5
tctttcctga gaaggagcag                                           20

<210> SEQ ID NO 6
<211> LENGTH: 20
<212> TYPE: DNA
<213> ORGANISM: Artificial sequence
<220> FEATURE:
<223> OTHER INFORMATION: MY07A reverse primer

<400> SEQUENCE: 6
atgggccgag ctttctttat                                           20

<210> SEQ ID NO 7
<211> LENGTH: 20
<212> TYPE: DNA
<213> ORGANISM: Artificial sequence
<220> FEATURE:
<223> OTHER INFORMATION: MY07A forward primer

<400> SEQUENCE: 7
cttctcttcc cccttgtgtg                                           20

<210> SEQ ID NO 8
<211> LENGTH: 20
<212> TYPE: DNA
<213> ORGANISM: Artificial sequence
<220> FEATURE:
<223> OTHER INFORMATION: MY07A reverse primer

<400> SEQUENCE: 8
cagagtcgca gagcttcacc                                           20

<210> SEQ ID NO 9
<211> LENGTH: 20
<212> TYPE: DNA
<213> ORGANISM: Artificial sequence
<220> FEATURE:
<223> OTHER INFORMATION: MY015 forward primer

<400> SEQUENCE: 9
cactccccaa cctgacatct                                           20

<210> SEQ ID NO 10
<211> LENGTH: 20
<212> TYPE: DNA
<213> ORGANISM: Artificial sequence

```
<220> FEATURE:
<223> OTHER INFORMATION: MY015 reverse primer

<400> SEQUENCE: 10
gctcagctcc tagagggaca                                            20

<210> SEQ ID NO 11
<211> LENGTH: 20
<212> TYPE: DNA
<213> ORGANISM: Artificial sequence
<220> FEATURE:
<223> OTHER INFORMATION: BDNF forward primer

<400> SEQUENCE: 11
gaggcttgac atcattggct                                            20

<210> SEQ ID NO 12
<211> LENGTH: 20
<212> TYPE: DNA
<213> ORGANISM: Artificial sequence
<220> FEATURE:
<223> OTHER INFORMATION: BDNF reverse primer

<400> SEQUENCE: 12
cgtgtacaag tctgcgtcct                                            20

<210> SEQ ID NO 13
<211> LENGTH: 23
<212> TYPE: DNA
<213> ORGANISM: Artificial sequence
<220> FEATURE:
<223> OTHER INFORMATION: NOS3 forward primer

<400> SEQUENCE: 13
gaccctggag atgaaggcag gag                                        23

<210> SEQ ID NO 14
<211> LENGTH: 24
<212> TYPE: DNA
<213> ORGANISM: Artificial sequence
<220> FEATURE:
<223> OTHER INFORMATION: NOS3 reverse primer

<400> SEQUENCE: 14
acctccagga tgttctagcg gtga                                       24

<210> SEQ ID NO 15
<211> LENGTH: 21
<212> TYPE: DNA
<213> ORGANISM: Artificial sequence
<220> FEATURE:
<223> OTHER INFORMATION: NOS3 forward primer

<400> SEQUENCE: 15
ccaggcccac cccaacctta t                                          21

<210> SEQ ID NO 16
<211> LENGTH: 20
<212> TYPE: DNA
<213> ORGANISM: Artificial sequence
<220> FEATURE:
<223> OTHER INFORMATION: NOS3 reverse primer

<400> SEQUENCE: 16
tcattcagtg acgcacgctt                                            20
```

```
<210> SEQ ID NO 17
<211> LENGTH: 20
<212> TYPE: DNA
<213> ORGANISM: Artificial sequence
<220> FEATURE:
<223> OTHER INFORMATION: NOS3 forward primer

<400> SEQUENCE: 17
cctggttatc aggccctatg                                               20

<210> SEQ ID NO 18
<211> LENGTH: 20
<212> TYPE: DNA
<213> ORGANISM: Artificial sequence
<220> FEATURE:
<223> OTHER INFORMATION: NOS3 reverse primer

<400> SEQUENCE: 18
aggctgctcc tgctactgac                                               20

<210> SEQ ID NO 19
<211> LENGTH: 23
<212> TYPE: DNA
<213> ORGANISM: Artificial sequence
<220> FEATURE:
<223> OTHER INFORMATION: GSTP1 forward primer

<400> SEQUENCE: 19
ctctatggga aggaccagca gga                                           23

<210> SEQ ID NO 20
<211> LENGTH: 21
<212> TYPE: DNA
<213> ORGANISM: Artificial sequence
<220> FEATURE:
<223> OTHER INFORMATION: GSTP1 reverse primer

<400> SEQUENCE: 20
caagccacct gaggggtaag g                                             21

<210> SEQ ID NO 21
<211> LENGTH: 22
<212> TYPE: DNA
<213> ORGANISM: Artificial sequence
<220> FEATURE:
<223> OTHER INFORMATION: GSTP1 forward primer

<400> SEQUENCE: 21
ttgacaggat ttggtactag cc                                            22

<210> SEQ ID NO 22
<211> LENGTH: 20
<212> TYPE: DNA
<213> ORGANISM: Artificial sequence
<220> FEATURE:
<223> OTHER INFORMATION: GSTP1 reverse primer

<400> SEQUENCE: 22
tggtctccca caatgaaggt                                               20

<210> SEQ ID NO 23
<211> LENGTH: 20
<212> TYPE: DNA
<213> ORGANISM: Artificial sequence
<220> FEATURE:
<223> OTHER INFORMATION: GSTM3 forward primer

<400> SEQUENCE: 23
```

```
cctcagtact tggaagagct                                               20

<210> SEQ ID NO 24
<211> LENGTH: 20
<212> TYPE: DNA
<213> ORGANISM: Artificial sequence
<220> FEATURE:
<223> OTHER INFORMATION: GSTM3 reverse primer

<400> SEQUENCE: 24
cacatgaaag ccttcaggtt                                               20

<210> SEQ ID NO 25
<211> LENGTH: 20
<212> TYPE: DNA
<213> ORGANISM: Artificial sequence
<220> FEATURE:
<223> OTHER INFORMATION: GSTZ1 forward primer

<400> SEQUENCE: 25
tgaccaccca gaagtggtag                                               20

<210> SEQ ID NO 26
<211> LENGTH: 20
<212> TYPE: DNA
<213> ORGANISM: Artificial sequence
<220> FEATURE:
<223> OTHER INFORMATION: GSTZ1 reverse primer

<400> SEQUENCE: 26
agtccacaag acacaggttc                                               20

<210> SEQ ID NO 27
<211> LENGTH: 20
<212> TYPE: DNA
<213> ORGANISM: Artificial sequence
<220> FEATURE:
<223> OTHER INFORMATION: GSTZ1 forward primer

<400> SEQUENCE: 27
tgaccaccca gaagtggtag                                               20

<210> SEQ ID NO 28
<211> LENGTH: 20
<212> TYPE: DNA
<213> ORGANISM: Artificial sequence
<220> FEATURE:
<223> OTHER INFORMATION: GSTZ1 reverse primer

<400> SEQUENCE: 28
agtccacaag acacaggttc                                               20
```